(12) United States Patent
Tilbrook et al.

(10) Patent No.: US 9,156,842 B2
(45) Date of Patent: Oct. 13, 2015

(54) PROCESS FOR PREPARING 3-[(4S)-8-BROMO-1-METHYL-6-(2-PYRIDINYL)-4H-IMIDAZO[1,2-A][1,4]BENZODIAZEPINE-4-YL]PROPIONIC ACID METHYL ESTER OR THE BENZENE SULFONATE SALT THEREOF, AND COMPOUNDS USEFUL IN THAT PROCESS

(75) Inventors: Gary Stuart Tilbrook, Bluntisham (GB); Andreas Schumacher, Efringen-Kirchen (DE); René Emmenegger, Basel (CH)

(73) Assignee: PAION UK LIMITED, Cambridge (GB)

( * ) Notice: Subject to any disclaimer, the term of this patent is extended or adjusted under 35 U.S.C. 154(b) by 507 days.

(21) Appl. No.: 13/496,742

(22) PCT Filed: Sep. 15, 2010

(86) PCT No.: PCT/EP2010/005668
§ 371 (c)(1),
(2), (4) Date: Aug. 30, 2012

(87) PCT Pub. No.: WO2011/032692
PCT Pub. Date: Mar. 24, 2011

(65) Prior Publication Data
US 2012/0330007 A1    Dec. 27, 2012

(30) Foreign Application Priority Data
Sep. 18, 2009   (EP) .................................. 09011914

(51) Int. Cl.
*C07D 487/04*   (2006.01)
*C07D 213/40*   (2006.01)
*C07D 401/04*   (2006.01)
*C07F 9/6558*   (2006.01)

(52) U.S. Cl.
CPC ............ *C07D 487/04* (2013.01); *C07D 213/40* (2013.01); *C07D 401/04* (2013.01); *C07F 9/65586* (2013.01)

(58) Field of Classification Search
CPC .................................................... C07D 487/04
USPC ........................................................ 540/562
See application file for complete search history.

(56) References Cited

U.S. PATENT DOCUMENTS 6,916,923 B2    7/2005    Ding et al.

FOREIGN PATENT DOCUMENTS

| JP | 2008/515991 | 5/2008 |
| JP | 2008/526984 | 7/2008 |
| RU | 2249593 | 4/2005 |
| WO | WO 00/69836 A1 | 11/2000 |
| WO | WO2006/044504 | 4/2006 |
| WO | WO 2006/078554 | 7/2006 |
| WO | WO 2008/007071 A1 | 1/2008 |
| WO | WO2008/147815 | 12/2008 |

OTHER PUBLICATIONS

P. Wipf: "I. Basic Principles ID, Oxidation Reaction", Apr. 2, 2006, XP002563124; Retrieved from the Internet: URL:ccc.chem.pitt.edu/wipf/Courses/2320_6-file; $2^{nd}$. Slide, p. 1, 5, 7.
"9-Fluorenylmethyl Carbamate, t-Butyl Carbamate" in: Greene, T.W.; Wuts, P.G.M.: "Protective Groups in Organic Synthesis" 1999, John Wiley & Sons Inc., New York, Chichester, Weinheim, Brisbane, Toronto, Singapore, XP002563125, ISBN: 0471160199, pp. 506, 518.

*Primary Examiner* — Brenda Coleman
(74) *Attorney, Agent, or Firm* — Henry M. Feiereisen LLC; Ursula B. Day

(57) ABSTRACT

The invention concerns a new process for preparing 3-[(4S)-8-bromo-1-methyl-6-(2-pyridinyl)-4H-imidazo[1,2-a][1,4]benzodiazepine-4-yl]-propionic acid methyl ester

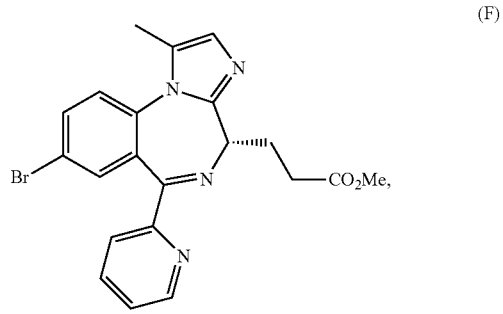

(F)

or
3-[(4S)-8-bromo-1-methyl-6-(2-pyridinyl)-4H-imidazo[1,2-a][1,4]benzodiazepine-4-yl]propionic acid methyl ester benzene sulfonate (P)
which comprises reacting 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM)

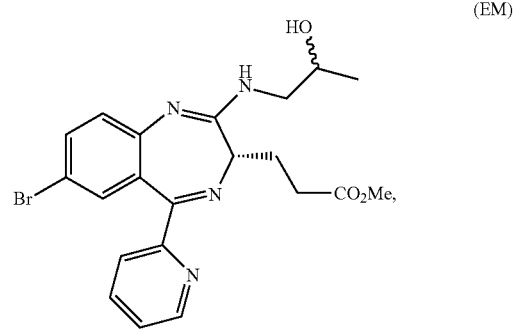

(EM)

with an oxidizing agent and optionally treating the reaction product under acidic conditions, such as to produce the compound of formula (F) or the compound (P), and new compounds useful as starting material or as intermediate for performing that process.

14 Claims, No Drawings

PROCESS FOR PREPARING 3-[(4S)-8-BROMO-1-METHYL-6-(2-PYRIDINYL)-4H-IMIDAZO[1,2-A][1,4]BENZODIAZEPINE-4-YL]PROPIONIC ACID METHYL ESTER OR THE BENZENE SULFONATE SALT THEREOF, AND COMPOUNDS USEFUL IN THAT PROCESS

CROSS-REFERENCES TO RELATED APPLICATIONS

This application is the U.S. National Stage of International Application No. PCT/EP20101005668, filed Sep. 15, 2010 which designated the United States and has been published as International Publication No, WO 2008/007071 and which claims the priority of European Patent Application, Serial No. 09011014.0 filed Sep. 18, 2009, pursuant to 35 U.S.C. 119 (a)-(d).

BACKGROUND OF THE INVENTION

The present invention relates to a process for preparing 3-[(4S)-8-bromo-1-methyl-6-(2-pyridinyl)-4H-imidazo[1,2-a][1,4]benzodiazepine-4-yl]-propionic acid methyl ester and the benzene sulfonate salt thereof, starting from 3-[(S)-7-Bromo-2-((R and/or S)-2-hydroxy-propylamino)-5-pyridin-2-yl-3H-benzo[e][1,4]diazepin-3-yl]-propionic acid methyl ester or 3-[(S)-7-Bromo-2-((R)-2-hydroxy-propylamino)-5-pyridin-2-yl-3H-benzo[e][1,4]diazepin-3-yl]-propionic acid methyl ester, and new compounds useful as starting material or intermediate in that process.

WO 00/69836 describes short-acting benzodiazepines that include a carboxylic ester moiety and are inactivated by non-specific tissue esterases. An organ-independent elimination mechanism is predicted to be characteristic of these benzodiazepines, providing a more predictable and reproducible pharmacodynamic profile. The compounds are suitable for therapeutic purposes, including sedative-hypnotic, anxiolytic, muscle relaxant and anticonvulsant purposes. The compounds are short-acting CNS depressants that are useful to be administered intravenously in the following clinical settings: preoperative sedation, anxiolysis, and amnestic use for perioperative events; conscious sedation during short diagnostic, operative or endoscopic procedures; as a component for the induction and maintenance of general anesthesia, prior and/or concomitant to the administration of other anaesthetic or analgesic agents; ICU sedation.

One of the compounds disclosed in that document is 3-[(4S)-8-bromo-1-methyl-6-(2-pyridinyl)-4H-imidazo[1,2-a][1,4]benzodiazepine-4-yl]-propionic acid methyl ester of formula (F) below

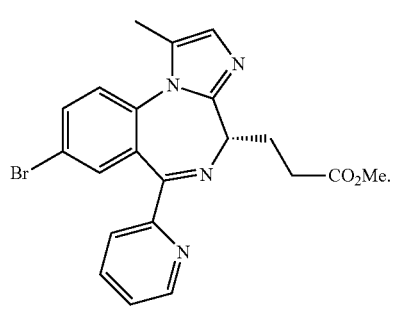

WO 00/69836 teaches a process for preparing the above compound of formula (F), which comprises:
(a) preparing 3-[(S)-7-bromo-2-oxo-5-pyridin-2-yl-2,3-dihydro-1H-1,4-benzodiazepin-3-yl]-propionic acid methyl ester of formula (D)

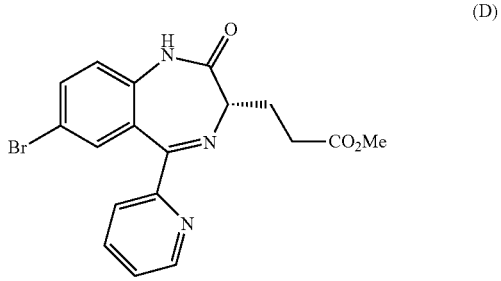 [SMILES: COC(=O)CC[C@@H]1N=C(c2ccccn2)c2cc(Br)ccc2NC1=O]

by reacting (2-amino-5-bromo-phenyl)-pyridin-2-yl-methanone of formula (A)

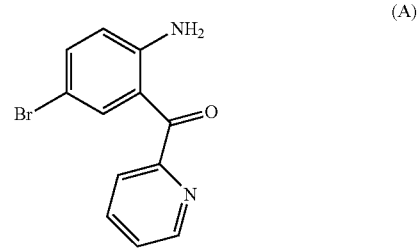 [SMILES: Nc1ccc(Br)cc1C(=O)c1ccccn1]

in chloroform with an alpha-Fmoc-protected-amino acid chloride (obtained by reacting FMOC-Glu(OMe)-OH and oxalylchloride in dichloromethane), treating the obtained amide with triethylamine in dichloromethane, then with acetic acid in 1,2-dichloroethane, isolating the compound of formula (D), and
(b) reacting the compound of formula (D) with a suspension of sodium hydride in THF, treating the reaction mixture with bis-morpholinophosphochloridate (BPMC) in THF, filtering the reaction mixture, reacting the filtrate with DL-1-amino-propanol, purifying the alcoholic adduct obtained, treating that purified alcoholic adduct with a mixture of DMSO and oxalyl chloride in dichloromethane, treating the reaction mixture with triethylamine, diluting with ethyl acetate, washing with aqueous solutions and concentrating to give a foam, treating that foam with a catalytic amount of p-toluenesulfonic acid, neutralizing the solution with sodium hydrogenocarbonate and isolating the compound of formula (F).

WO 2008/007071 discloses a method of preparing the besylate salt (P) of the above compound of formula (F) by adding benzene sulfonic acid to a solution of that compound in toluene or ethyl acetate, stirring, filtering, washing with toluene or ethyl acetate and drying under vacuum. That method yields 3-[(4S)-8-Bromo-1-methyl-6-(2-pyridinyl)-4H-imidazo[1,2-a][1,4]benzodiazepine-4-yl]propionic acid methyl ester benzene sulfonate (P) which is taught to be a particularly interesting active pharmaceutical ingredient (API).

The process for preparing the direct precursor of that API, namely 3-[(4S)-8-bromo-1-methyl-6-(2-pyridinyl)-4H-imidazo[1,2-a][1,4]benzodiazepine-4-yl]propionic acid methyl ester of formula (F), or that API, 3-[(4S)-8-Bromo-1-methyl-6-(2-pyridinyl)-4H-imidazo[1,2-a][1,4]benzodiazepine-4-yl]propionic acid methyl ester benzene sulfonate (P), starting from the compound of formula (A) disclosed in WO 00/69836 is not satisfying for an industrial preparation, notably because of the high number of steps, the low overall yield and the insufficient optical purity of the compounds obtained at the different steps.

The objective of the invention is to find a process for preparing compound (P) and precursors thereof that does not have the above drawbacks.

That objective is attained by the invention as defined in the appended claims.

SUMMARY OF THE INVENTION

The process of the invention thus relates to a new method for preparing the compound of formula (F) or its besylate salt (P), comprising oxidizing 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM)

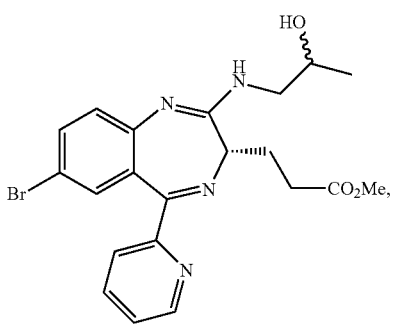

(EM)

or in a preferred embodiment oxidizing 3-[(S)-7-bromo-2-((R)-2-hydroxy-propylamino)-5-pyridin-2-yl-3H-benzo[e][1,4]diazepin-3-yl]-propionic acid methyl ester of formula (E)

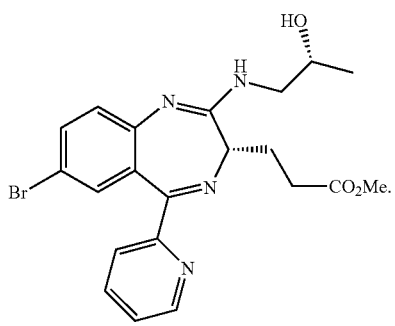

(E)

That method allows to obtain 3-[(4S)-8-bromo-1-methyl-6-(2-pyridinyl)-4H-imidazo[1,2-a][1,4]benzodiazepine-4-yl]propionic acid methyl ester of formula (F) or its besylate salt (P), namely 3-[(4S)-8-Bromo-1-methyl-6-(2-pyridinyl)-4H-imidazo[1,2-a][1,4]benzodiazepine-4-yl]propionic acid methyl ester benzene sulfonate, with very high chemical and chiral purities.

The process of the invention may include steps for preparing 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM) starting from one of the precursors of the compound of formula (F) disclosed in WO 00/69836, namely 3-[(S)-7-bromo-2-oxo-5-pyridin-2-yl-2,3-dihydro-1H-1,4-benzodiazepin-3-yl]-propionic acid methyl ester of formula (D) or (2-amino-5-bromo-phenyl)-pyridin-2-yl-methanone of formula (A).

It then provides a process for preparing 3-[(4S)-8-bromo-1-methyl-6-(2-pyridinyl)-4H-imidazo[1,2-a][1,4]benzodiazepine-4-yl]propionic acid methyl ester of formula (F) or 3-[(4S)-8-Bromo-1-methyl-6-(2-pyridinyl)-4H-imidazo[1,2-a][1,4]benzodiazepine-4-yl]propionic acid methyl ester benzene sulfonate (P), with very high chemical and chiral purities, which has less steps, a better reproducibility and a better overall yield with regard to the compound of formula (D) or the compound of formula (A) than the process disclosed in WO 00/69836.

The invention concerns a process for preparing 3-[(4S)-8-bromo-1-methyl-6-(2-pyridinyl)-4H-imidazo[1,2-a][1,4]benzodiazepine-4-yl]propionic acid methyl ester of formula (F)

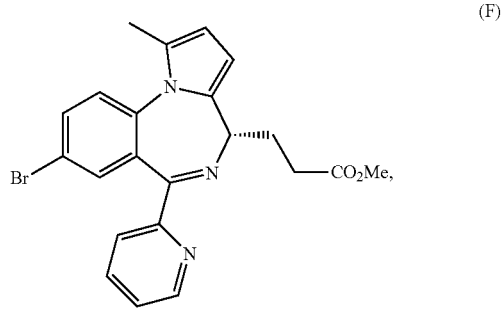 [SMILES: COC(=O)CC[C@@H]1N=C(c2ccccn2)c2cc(Br)ccc2-n2c(C)ccc21]

(F)

which comprises reacting 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM)

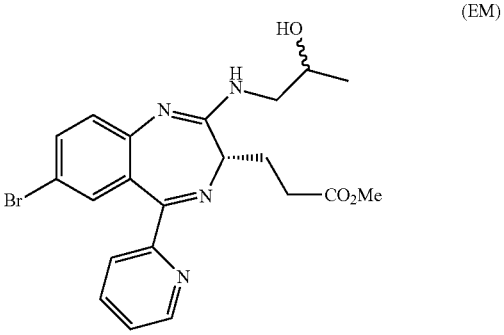 [SMILES: COC(=O)CC[C@@H]1N=C(c2ccccn2)c2cc(Br)ccc2N=C1NCC(C)O]

(EM)

with an oxidizing agent and optionally treating the reaction product under acidic conditions, such as to produce the compound of formula (F).

The compound of formula (EM) may be 3-[(S)-7-bromo-2-((R)-2-hydroxy-propylamino)-5-pyridin-2-yl-3H-benzo[e][1,4]diazepin-3-yl]-propionic acid methyl ester of formula (E)

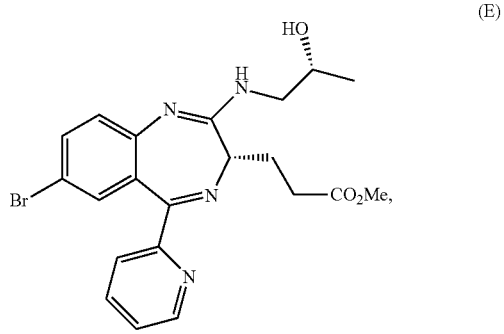 [SMILES: COC(=O)CC[C@@H]1N=C(c2ccccn2)c2cc(Br)ccc2N=C1NC[C@@H](C)O]

(E)

3-[(S)-7-bromo-2-((S)-2-hydroxy-propylamino)-5-pyridin-2-yl-3H-benzo[e][1,4]diazepin-3-yl]-propionic acid methyl ester of formula (E)

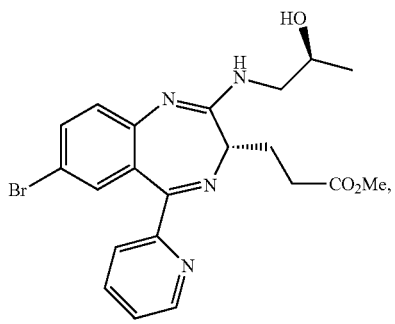

(E')

or a mixture of the compounds of formula (E) and (E').

Preferably the compound of formula (EM) is a compound of formula (E).

The compound of the formula (EM) can be obtained by reacting in an aprotic solvent the compound of formula (E1) with (R)-1-amino-2-propanol or (S)-1-amino-2-propanol, both compounds are commercially available.

In one embodiment in step (b) the compound of formula (E1) can be reacted with (S)-1-amino-2-propanol, yielding 3-[(S)-7-bromo-2-((S)-2-hydroxy-propylamino)-5-pyridin-2-yl-3H-benzo[e][1,4]diazepin-3-yl]-propionic acid methyl ester of formula (E').

Preferably in step (b) the compound of formula (E1) is reacted with (R)-1-amino-2-propanol, yielding the preferred 3-[(S)-7-bromo-2-((R)-2-hydroxy-propylamino)-5-pyridin-2-O-3H-benzo[e][1,4]diazepin-3-yl]-propionic acid methyl ester of formula (E).

The optical purity of the compounds of formula (E) and (E') depends on the purity of the 1-amino-2-propanol used in the synthesis. For the purposes of the present invention it is preferred to obtain the compound of the formula (E) at an optical purity of ≥95%, preferably ≥99%, and more preferably ≥99.5%, using (R)-1-amino-2-propanol.

The oxidizing agent is an agent apt to oxidize a secondary alcohol to a ketone without reacting with the other reactive groups of the compound of formula (EM).

Examples of suitable oxidizing agents are sulfonated pyridine in dimethylsulfoxide (DMSO) in presence of a base such as diisopropylethylamine (DIEA), oxalyl chloride in DMSO in presence of a base such as triethylamine, Albright-Goldman oxidation reagent (acetic acid anhydride/DMSO), S-IBX oxidation reagent (1-Hydroxy-(1H)-benzo-1,2-iodoxol-3-one-1-oxide), a combination of hypochlorite and a catalytic amount of tetramethylpiperidine-1-oxyl (TEMPO), and a hypervalent iodine compound of formula (DM)

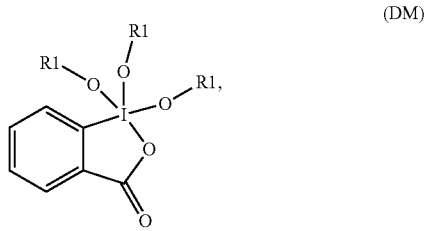

(DM)

wherein R1 is acyl, preferably $C_2$-$C_{10}$ acyl, more preferably $C_2$-$C_4$ acyl, such as 1,1,1-triacetoxy-1,1-dihydro-1,2-benziodoxol-3(1H)-one (Dess-Martin periodinane).

The oxidizing agent may convert the compound of formula (EM) directly to the compound of formula (F), or to the intermediate ketone of formula

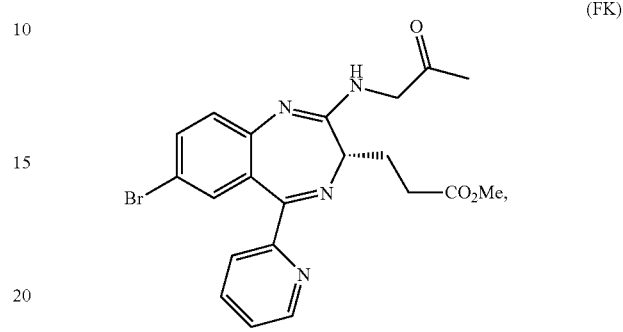

(FK)

which can then be cyclized under acidic conditions into the compound of formula (F).

The compound of formula (F) may be isolated by methods routinely used in the art of synthetic organic chemistry, which may e.g. include evaporating the solvent under vacuum, dissolving the residue in a suitable solvent, filtering, washing with different aqueous solutions and re-extracting the combined aqueous solutions with a suitable solvent.

For the purposes of the present invention it is preferred to obtain the compound of the formula (F) at an optical purity of ≥95%, preferably ≥99%, more preferably ≥99.5%, and most preferably >99.9%.

A preferred oxidizing agent is an hypervalent iodine compound of formula (DM)

(DM)

wherein R1 is acyl, preferably $C_2$-$C_{10}$ acyl, in particular $C_2$-$C_4$ acyl.

Most preferably R1 is acetyl, the compound of formula (DM) then being 1,1,1-triacetoxy-1,1-dihydro-1,2-benzoiodoxol-3(1H)-one) (Dess-Martin periodinane).

Where the oxidizing agent is Dess-Martin periodinane, the reaction is generally performed by treating the compound of formula (EM) with a stoichiometric excess, usually from 1.0 to 2.0, preferably 1.2 to 1.8, particularly 1.4 to 1.6 equivalent of Dess-Martin periodinane, in an aprotic solvent such as e.g. dichloromethane, chloroform, acetonitrile, tetrahydrofuran or butanone. Particularly good results have been obtained in butanone.

The Dess-Martin periodinane is conveniently added in solid form and in portions to a solution of the compound of formula (EM) in an aprotic solvent.

Where the aprotic solvent is butanone, the reaction is preferably carried out at a temperature between 30 and 45° C.

Where the oxidizing agent is Dess-Martin periodinane, the reaction product mainly contains the compound of formula (F) and there is generally no further acidic reaction performed.

The compound of formula (F) may be isolated by methods routinely used in the art of synthetic organic chemistry, which may e.g. include evaporating the solvent under vacuum, dissolving the residue in a suitable solvent, filtering, washing with different aqueous solutions and re-extracting the combined aqueous solutions with a suitable solvent.

Another interesting oxidizing agent is a combination of a catalytic amount of tetramethylpiperidine-1-oxyl (TEMPO) and hypochlorite.

The compound of formula (EM) is generally treated in solution with a catalytic amount of TEMPO, e.g. 0.005 to 0.03 equivalent of TEMPO, and 1.0 to 1.8 equivalent of hypochlorite, usually in a solvent or a solvent mixture which contains water having a pH 6.0 to 8.0, the pH being adjusted if necessary by adding additives such as e.g. hydrogen carbonate or acetic acid, and a salt such as sodium or potassium bromide. A suitable solvent mixture is e.g. ethyl acetate/toluene/water or dichloromethane/water.

Where the oxidizing agent is a combination of a catalytic amount of TEMPO and hypochlorite, the reaction product mainly contains 3-[(S)-7-bromo-2-(2-oxo-propylamino)-5-pyridin-2-yl-3H-1,4-benzodiazepin-3-yl]-propionic acid methyl ester of formula (FK)

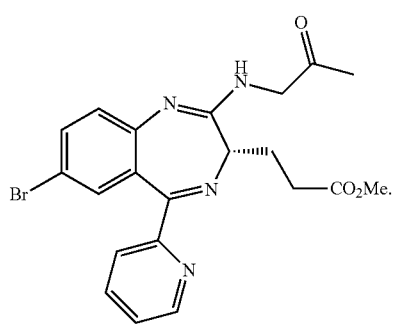

(FK)

That compound can be cyclized into the compound of formula (F) under acidic conditions.

Suitable acidic conditions are generally an organic acid in an organic solvent.

Examples of suitable acidic conditions are p-toluene sulfonic acid in chloroform or a mixture of benzene sulfonic acid in substantially less than the stoichiometric amount (preferably less than a fifth of the stoichiometric amount, more preferably about a tenth of the stoichiometric amount) and molecular sieve MS3A in dichloromethane.

The compound of formula (F) may be isolated by methods routinely used in the art of synthetic organic chemistry, which may e.g. include evaporating the solvent under vacuum, dissolving the residue in a suitable solvent, filtering, washing with different aqueous solutions and re-extracting the combined aqueous solutions with a suitable solvent.

The invention also concerns a process for preparing the besylate salt 3-[(4S)-8-bromo-1-methyl-6-(2-pyridinyl)-4H-imidazo[1,2-a][1,4]benzodiazepine-4-yl]propionic acid methyl ester benzene sulfonate (P) which comprises
(a) reacting 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM)

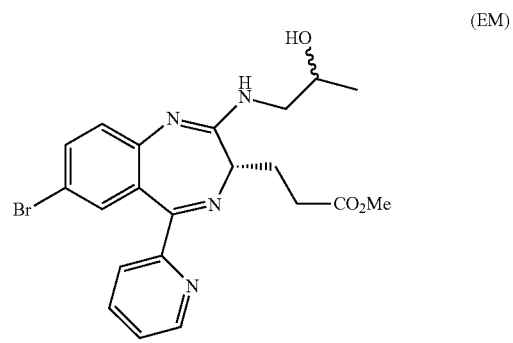

(EM)

with an oxidizing agent, and
(b) treating the reaction product obtained in step (a) with benzene sulfonic in an organic solvent or an organic solvent mixture, such as to produce the compound (P).

The compound (P) may be isolated by methods routinely used in the art of synthetic organic chemistry, which may e.g. include crystallisation of the besylate salt.

For the purposes of the present invention it is preferred to obtain the compound of the formula (P) at an optical purity of ≥95%, preferably ≥99%, more preferably ≥99.5%, and most preferably >99.9%.

Preferably the compound of formula (EM) is a compound of formula (E).

In a preferred embodiment the oxidation agent is a combination of hypochlorite and a catalytic amount of TEMPO, whereby the compound of formula (EM) is treated in solution with 0.005 to 0.03 equivalent of TEMPO and 1.0 to 1.8 equivalent of hypochlorite, such as to give 3-[(S)-7-bromo-2-(2-oxo-propylamino)-5-pyridin-2-yl-3H-1,4-benzodiazepin-3-yl]-propionic acid methyl ester of formula (FK)

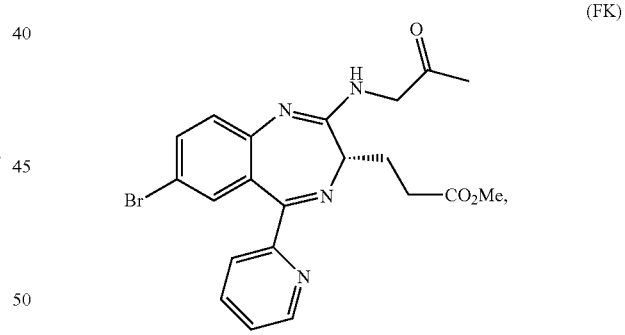

(FK)

and
(b) treating the compound of formula (FK) with benzene sulfonic acid in an organic solvent or an organic solvent mixture, such as to produce the compound (P).

The organic solvent or the organic solvent mixture used in step (b) is an organic solvent capable of favouring in presence of benzene sulfonic acid the cyclization of the 3-[(S)-7-bromo-2-(2-oxo-propylamino)-5-pyridin-2-yl-3H-1,4-benzodiazepin-3-yl]-propionic acid methyl ester of formula (FK), the formation of the benzene sulfonate salt and optionally the crystallisation of that salt.

Examples of suitable organic solvent mixtures are ethyl acetate and ethanol, ethyl acetate and 2-propanol, and ethyl acetate and methanol.

A preferred organic solvent mixture is ethyl acetate and ethanol.

3-[(S)-7-bromo-2-((R and/or S)-2-hydroxy-propylamino)-5-pyridin-2-yl-3H-benzo[e][1,4]diazepin-3-yl]-propionic acid methyl ester of formula (EM) used as starting material in the above defined process for preparing 3-[(4S)-8-bromo-1-methyl-6-(2-pyridinyl)-4H-imidazo[1,2-a][1,4]benzodiazepine-4-yl]propionic acid methyl ester of formula (F) or 3-[(4S)-8-bromo-1-methyl-6-(2-pyridinyl)-4H-imidazo[1,2-a][1,4]benzodiazepine-4-yl]propionic acid methyl ester benzene sulfonate (P), may be prepared by a method comprising (a) reacting 3-[(S)-7-bromo-2-oxo-5-pyridin-2-yl-2,3-dihydro-1H-1,4-benzodiazepin-3-yl]-propionic acid methyl ester of formula (D)

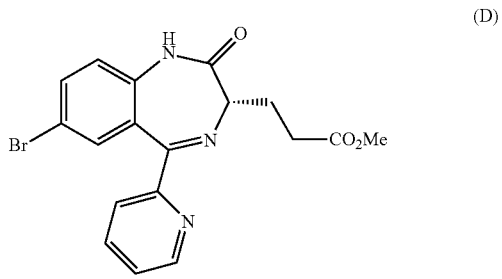 [SMILES: COC(=O)CC[C@@H]1N=C(c2ccccn2)c2cc(Br)ccc2NC1=O]

(D)

with lithium diisopropylamide (LDA) and bis-morpholinophosphorylchloridate (BMPC), such as to give the compound of formula (E1),

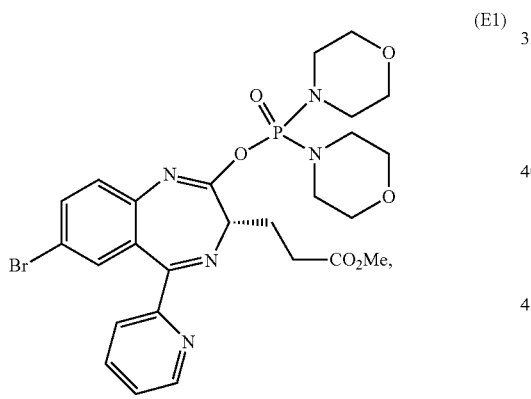

(E1)

and (b) reacting the compound of formula (E1) with (R)-1-amino-2-propanol or (S)-1-amino-2-propanol.

Step (a) is generally performed by dissolving the compound of formula (D) in an aprotic solvent and adding LDA and BMPC. Usually LDA is added prior to BMPC. The skilled person would also consider adding BMPC prior to LDA as being a suitable alternative.

A suitable aprotic solvent is for instance tetrahydrofurane (THF), a mixture of THF with an alkane solvent (e.g. heptane) and an aralkane solvent (e.g. ethylbenzene), or an ether, e.g. diethyl ether.

Generally 1.0 to 1.5 equivalent of LDA and at least 1.5 equivalents of BMPC are used.

Preferably 1.0 to 1.2, in particular 1.0 to 1.1, equivalent of LDA and at least 2.0 equivalents of BMPC are used.

Step (b) is generally carried out by reacting in an aprotic solvent the compound of formula (E1) with (R)-1-amino-2-propanol or (S)-1-amino-2-propanol to yield the compound of the formula (EM).

In one embodiment in step (b) the compound of formula (E1) can be reacted with (S)-1-amino-2-propanol, yielding 3-[(S)-7-bromo-2-((S)-2-hydroxy-propylamino)-5-pyridin-2-yl-3H-benzo[e][1,4]diazepin-3-yl]propionic acid methyl ester of formula (E').

Preferably in step (b) the compound of formula (E1) is reacted with (R)-1-amino-2-propanol, yielding the preferred 3-[(S)-7-bromo-2-((R)-2-hydroxy-propylamino)-5-pyridin-2-yl-3H-benzo[e][1,4]diazepin-3-yl]-propionic acid methyl ester of formula (E).

An example of a suitable aprotic solvent is THF, a mixture of THF with an alkane solvent (e.g. heptane) and an aralkane solvent (e.g. ethylbenzene), or an ether, e.g. ethyl ether.

3-[(S)-7-bromo-2-((R)-2-hydroxy-propylamino)-5-pyridin-2-yl-3H-benzo[e][1,4]diazepin-3-yl]-propionic acid methyl ester of formula (EM) is usually isolated and purified by recrystallisation from a suitable solvent, preferably one selected from the group of ethyl acetate, isobutylacetate, 2-propanol, toluene, or ethyl acetate/heptane.

3-[(S)-7-bromo-2-oxo-5-pyridin-2-yl-2,3-dihydro-1H-1,4-benzodiazepin-3-yl]-propionic acid methyl ester of formula (D) used above as starting material for preparing 3-[(S)-7-bromo-2-((R)-2-hydroxy-propylamino)-5-pyridin-2-yl-3H-benzo[e][1,4]diazepin-3-yl]-propionic acid methyl ester of formula (EM), may be prepared by a method comprising cyclizing the compound of formula (C)

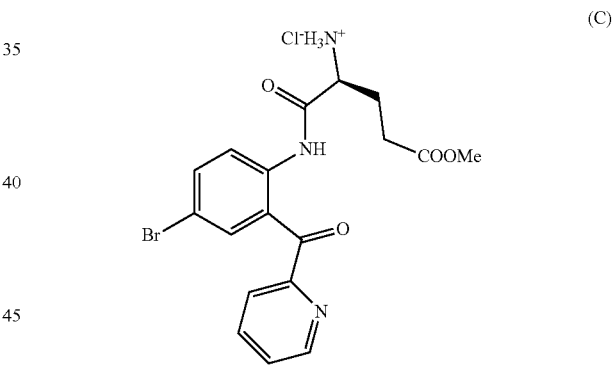

(C)

by treatment with a base in an organic solvent or organic solvent mixture.

A suitable organic solvent is for instance THF, DMF, acetonitrile or methanol.

A suitable base is for instance an alkaline metal hydrogen carbonate, e.g. sodium hydrogen carbonate, or a tertiary amine, e.g. triethylamine, diisopropylethylamine, N,N-dimethylaniline and pyridine.

3-[(S)-7-bromo-2-oxo-5-pyridin-2-yl-2,3-dihydro-1H-1,4-benzodiazepin-3-yl]-propionic acid methyl ester of formula (D) may be purified by recrystallisation from a secondary alcoholic solvent, e.g. isopropanol or isobutanol, preferably isopropanol, or a solvent mixture such as e.g. ethyl acetate/heptane.

The compound of formula (C) used above as starting material for preparing 3-[(S)-7-bromo-2-oxo-5-pyridin-2-yl-2,3-dihydro-1H-1,4-benzodiazepin-3-yl]-propionic acid methyl ester of formula (D), may be prepared by cleaving the 'Boc group of the compound of formula (B)

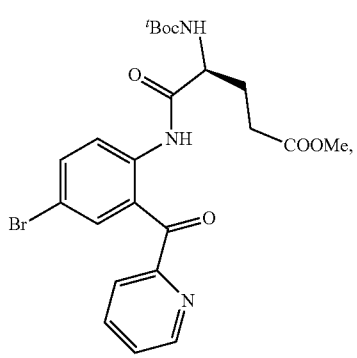
(B)

by treatment with hydrogen chloride.

The reaction may be performed by dissolving the compound of formula (B) in a polar solvent such as ethanol or methanol, adding hydrogen chloride in 1,4-dioxane and preferably cooling the reaction mixture.

The compound of formula (B) used above as starting material for preparing the compound of formula (C) may be prepared by treating (2-amino-5-bromo-phenyl)-pyridin-2-yl-methanone of formula (A)

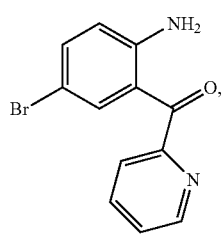
(A)

with ᵗBoc-Glu(OMe)-OH in an organic solvent in presence of a coupling agent.

A suitable organic solvent is for instance THF, DMF, dichloromethane or ethyl acetate.

Suitable coupling agents include those selected from the group consisting of Dicyclohexylcarbodiimide (DCC), N,N,N',N'-Tetramethyl-O-(7-azabenzotriazol-1-yl)uronium hexafluorophosphate (HATU), 2-(1H-Benzotriazole-1-yl)-1,1,3,3-tetramethyluronium hexafluorophosphate (HBTU), 1-Ethyl-3-(3-dimethylaminopropyl)-carbodiimide (EDC), propane phosphonic acid anhydride T3P, Benzotriazol-1-yl-oxytripyrrolidinophosphonium hexafluorophosphate PyBOP, isobutylchloroformate, carbonyldiimidazole (CDI), chlorenamine, or N,N'-diisopropylcarbodiimide (DIC).

Depending on the coupling agent, a base such as e.g. diisopropylethylamine (DIEA), triethylamine (TEA) or N-methylmorpholine (NMM), or another additive may be used.

A preferred coupling agent is DCC, e.g. in dichloromethane or dimethylformamide (DMF).

The invention also concerns a new compound useful as starting material or intermediate for performing the above defined process for preparing 3-[(4S)-8-bromo-1-methyl-6-(2-pyridinyl)-4H-imidazo[1,2-a][1,4]benzodiazepine-4-yl] propionic acid methyl ester of formula (F) or 3-[(4S)-8-bromo-1-methyl-6-(2-pyridinyl)-4H-imidazo[1,2-a][1,4] benzodiazepine-4-yl]propionic acid methyl ester benzene sulfonate (P), which is selected from the group consisting of a) 3-[(S)-7-Bromo-2-((R)-2-hydroxy-propylamino)-5-pyridin-2-yl-3H benzo[e][1,4]diazepin-3-yl]-propionic acid methyl ester of formula (E)

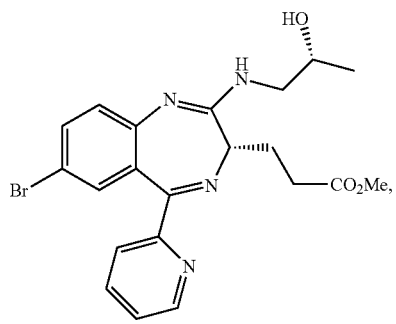
(E)

b) 3-[(S)-7-Bromo-2-(2-oxo-propylamino)-5-pyridin-2-yl-3H-1,4-benzodiazepin-3-yl]-propionic acid methyl ester of formula (FK)

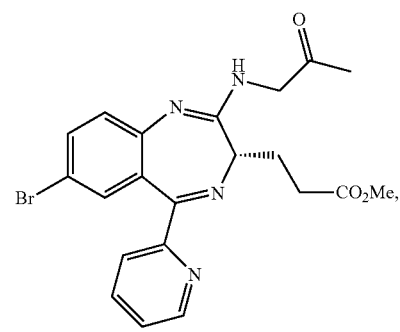
(FK)

c) the compound of formula (E1)

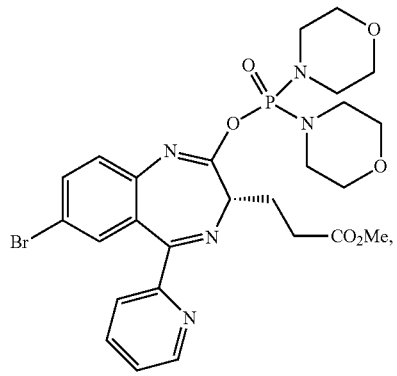
(E1)

d) the compound of formula (C)

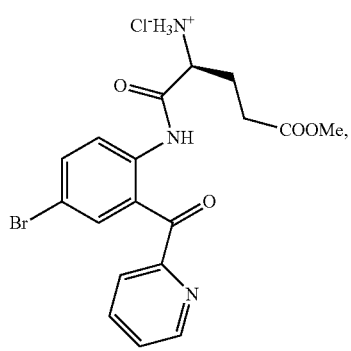
(C)

or e) the compound of formula (B)

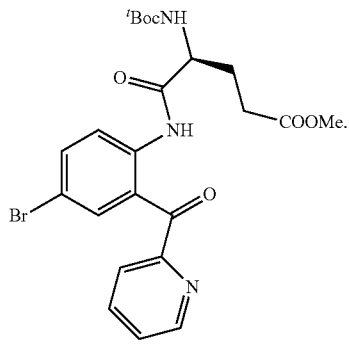

The invention also relates to the use of the compounds of the formula (EM), (E), (E1), (FK), (C), (B) in the preparation of a compound of the formula (F) or its besylate salt (P), and also the use of the above defined process for preparing 3-[(4S)-8-bromo-1-methyl-6-(2-pyridinyl)-4H-imidazo[1,2-a][1,4]benzodiazepine-4-yl]propionic acid methyl ester of formula (F), in the preparation of 3-[(4S)-8-bromo-1-methyl-6-(2-pyridinyl)-4H-imidazo[1,2-a][1,4]benzodiazepine-4-yl]propionic acid methyl ester benzene sulfonate (P), whereby the 3-[(4S)-8-bromo-1-methyl-6-(2-pyridinyl)-4H-imidazo[1,2-a][1,4]benzodiazepine-4-yl]propionic acid methyl ester of formula (F) is treated with benzene sulfonic acid in a solvent or a solvent mixture, preferably selected from the group consisting of ethanol, 2-propanol, ethanol/ethyl acetate, 2-propanol/ethyl acetate and methanol/ethyl acetate. The formed besylate salt (P) is then optionally crystallized from that solvent or solvent mixture.

The following examples illustrate the invention.

DETAILED DESCRIPTION OF PREFERRED EMBODIMENTS

EXAMPLE A1

Preparation of the Compound of Formula (B)

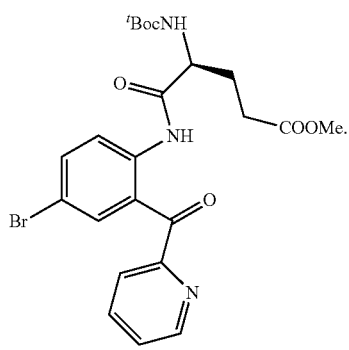

222 g (801 mmol) (2-amino-5-bromo-phenyl)-pyridin-2-yl-methanone of formula (A)

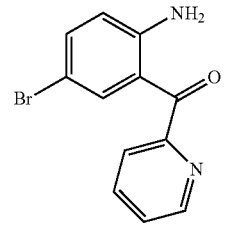

(prepared as described in European Journal of Organic Chemistry, 2006, 13, 2987-2990) and 230 g (881 mmol) $^t$Boc-Glu(OMe)-OH were mixed as solids and dissolved in 1200 ml dichloromethane and the solution was cooled to a temperature of −10° C. A solution of coupling reagent dicyclohexylcarbodiimide DCC (165 g, 801 mmol) in 400 ml dichloromethane was added dropwise over a period of 1 hour while the internal temperature was kept at a temperature from −10° C. to −5° C., then the solution was stirred for 40 hours at a temperature of −5° C. to 0° C. The suspension was filtered, the filter cake was washed with 1000 ml dichloromethane and the filtrate was evaporated to a yellow residue, showing for the main product the following NMR data:

1H-NMR (CDCl3, 300 MHz) 11.29 (brs, 1H); 8.65 (dt, 1H, J=4.8, 1.4); 8.50 (d, 1H, J=9.0); 7.91 (d, 1H, J=2.3); 7.86 (m, 2H); 7.59 (dd, 1H, J=9.0, 2.3) 7.45 (ddd, 1H, J=6.4, 4.0, 2.3); 5.27 (brd, 1H, J=6.4); 4.27 (brm, 1H); 3.60 (s, 3H); 2.52-2.14 (m, 2H); 2.04-1.82 (m, 2H); 1.36 (s, 9H), corresponding to the compound of formula (B).

EXAMPLE A2

Preparation of the Compound of Formula (C)

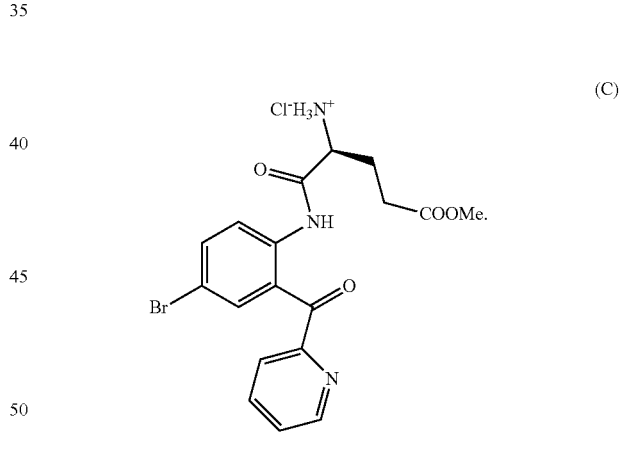

The compound of formula (B) (1833 g, 2642 mmol) was dissolved in 2200 ml methanol at room temperature. The solution was transferred into a 10 l reactor and cooled to a temperature below 20° C. To this solution hydrogen chloride (11200 mmol) in 2800 ml 1,4-dioxane was added over a period of 15 minutes while maintaining the reaction mixture at a temperature of 15 to 10° C. The mixture was stirred for 3 hours at a temperature of 15 to 10° C. The solution obtained was directly used in Example A3 below. That solution showed for the main product the following NMR data:

1H-NMR (CDCl3, 300 MHz) 11.23 (brs, 1H); 8.63 (dt, 1H, J=4.6, 1.3); 8.36 (brd, 2H, J=4.3); 8.06 (d, 1H, J=1.3); 8.0 (m, 1H); 7.78 (dd, 1H, J=8.6, 2.4) 7.64 (m, 2H) 7.46 (d, 1H, 8.6); 4.00 (brm, 1H); 3.62 (s, 3H); 2.41-2.23 (m, 2H); 1.83-1.56 (m, 2H), corresponding to the compound of formula (C).

EXAMPLE A3

Preparation of 3-[(S)-7-bromo-2-oxo-5-pyridin-2-yl-2,3-dihydro-1H-1,4-benzodiazepin-3-yl]-propionic acid methyl ester of formula (D)

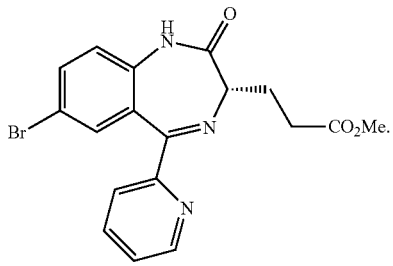
(D)

449 g (5343 mmol) of sodium hydrogen carbonate were suspended in 2000 ml of acetonitrile under vigorous stirring. The solution of the compound of formula (C) obtained in Example A2 above (1743 g, 763 mmol) was added to that suspension in 4 equal portions at room temperature over a period of 30 minutes (actual solvent ratio methanol/1,4-dioxane/acetonitrile:3/4/10). The temperature decreased to 15° C., with an intensive gas development and a slight foaming after addition of each portion. The colour switched after each addition from orange (colour of the hydrochloric solution) to yellow-green. The yellow-green solution was stirred at a temperature of about 15° C. for 3 hours 40 minutes. The reaction mixture was filtered over a thin layer of celite, washed with acetonitrile and evaporated in vacuo at 50° C. bath temperature, yielding 424 g of viscous resin, The resin was dissolved in 1500 ml of 2-propanol at 85° C. After cooling the precipitated solid was isolated by filtration and washed with 2-propanol and dried at a temperature of 35° C. in vacuo to give the product as a yellow crystalline solid (215.8 g, 528 mmol) having the following NMR data:

1H-NMR (CDCl3, 300 MHz) 8.69 (s, 1H); 8.52 (dq, 1H, J=4.8, 1.6, 0.8); 7.99 (dt, 1H, J=8.0, 1.0); 7.73 (td, 1H J=7.8, 1.8); 7.54-7.43 (m, 2H) 7.28 (qd, 1H, J=7.6, 4.8, 1.0); 6.93 (d, 1H, J=8.6); 3.67 (dd, 1H J=7.6, 6.1); 3.60 (s, 3H) 2.66-2.34 (m, 4H), corresponding to the compound of formula (D).

For the process described in Examples A1 to A3, the overall yield from (2-amino-5-bromo-phenyl)-pyridin-2-yl-methanone of formula (A) to 3-[(S)-7-bromo-2-oxo-5-pyridin-2-yl-2,3-dihydro-1H-1,4-benzodiazepin-3-yl]-propionic acid methyl ester of formula (D) is about 67%. The chemical purity of the isolated solid as determined by HPLC (at 230 nm) was 98.35% and its optical (chiral) purity determined by HPLC (at 290 nm) was 100%.

EXAMPLE A4

Preparation of 3-[(S)-7-bromo-2-oxo-5-pyridin-2-yl-2,3-dihydro-1H-1,4-benzodiazepin-3-yl]-propionic acid methyl ester of formula (E)

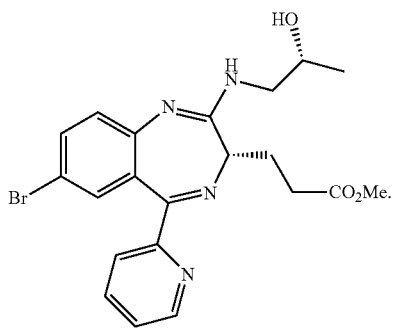
(E)

1.36 kg (3.39 mol) compound of formula (D) was suspended in 3500 ml dry tetrahydrofurane (THF) under argon and cooled down to −18° C. A 2M solution of lithium diisopropylamide LDA (3.4 mol) in 1700 ml THF/heptane/ethylbenzene was added over a period of 90 minutes. The addition was exothermic and the temperature was controlled to be between −10 and −5° C. The mixture was then stirred for 105 minutes at 0° C., followed by the portionwise addition of bis-morpholinophosphoryl-chloridate BMPC (1.74 kg; 6.78 mol) over 15 minutes. The brown suspension was stirred for 150 minutes and the temperature held between −5 and 0° C. An analytical amount of the main product isolated by chromatography was found to have the following NMR data:

1H-NMR (CDCl3, 300 MHz) 8.68 (ddd, 1H, J=4.8, 1.7, 0.9); 7.96 (dt, 1H, J=7.9, 1.0); 7.8 (td, 1H, J=7.7, 1.8); 7.67 (dd, 1H, J=8.6, 2.3); 7.57 (d, 1H, J=2.0); 7.41 (ddd, 1H, J=7.5, 4.8, 1.2); 7.36 (d, 1H, J=8.6); 7.2 (m, 1H); 3.85-3.65 (m, 8H+3H) 3.33-3.19 (m, 8H); 2.76-2.45 (m, 4H), corresponding to the compound of formula (E1))

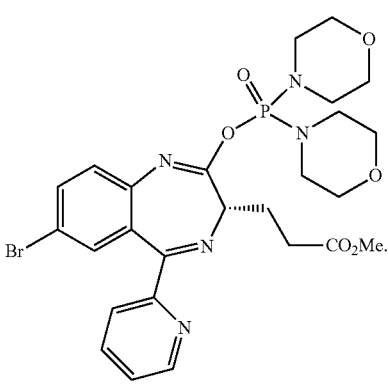
(E1)

A solution of (R)-1-amino-2-propanol (519 g; 6.91 mol) in dry THF (1500 ml) was added within 105 minutes and the temperature was kept between +4 and −2° C. The mixture was stirred for 16 hours at room temperature. A second addition of the (R)-1-amino-2-propanol (102 g; 1.36 mol) in dry THF (150 ml) was carried out within 5 minutes. It was stirred for another 25 hours, then evaporated widely.

To the pasty residue were added dichloromethane (5 l) and saturated aqueous sodium bicarbonate solution (5 l). The layers were separated. The organic layer was washed with saturated aqueous ammonium chloride solution (2.5 l) and water (2 l). Each aqueous layer was re-extracted with dichloromethane (200 ml). The combined organic layers were dried over sodium sulfate, filtered and evaporated. The crude product was recrystallised from 95° C. hot toluene after slow cooling and filtration as a yellowish solid in 56% yield (876 g) with the following NMR data:

1H-NMR (CDCl3, 300 MHz) 8.6 (ddd, 1H, J=4.8, 1.6, 1.0); 7.87 (dm, 1H, J=7.8); 7.79 (td, 1H, J=7.5, 1.7); 7.51 (dd, 1H, J=8.7, 2.3); 7.39 (d, 1H, J=2.3); 7.36 (ddd, 1H, J=7.4, 2.5, 1.4); 7.13 (d, 1H, J=8.8); 5.76 (tb, 1H) 5.19 (b, 1H); 3.98 (m, 1H) 3.71 (s, 3H); 3.5-3.2 (m, 3H) 2.9-2.3 (m, 4H); 1.17 (d, 3H, J=6.3), corresponding to the compound of formula (E). Chemical purity as determined by HPLC (254 nm) was 98.77%. The optical purity as determined by HPLC (290 nm) was 99.54%.

EXAMPLE A5

Preparation of 3-[(4S)-8-bromo-1-methyl-6-(2-pyridinyl)-4H-imidazo[1,2-a][1,4]benzodiazepine-4-yl] propionic acid methyl ester of formula (F) using Dess-Martin periodinane as oxidizing agent

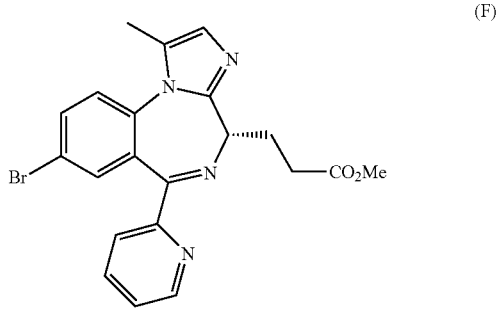 [SMILES: COC(=O)CC[C@@H]1N=C(c2ccccn2)c2cc(Br)ccc2-n2c(C)cnc21]

(F)

The compound of formula (E) (874 g, 1.9 mol) was dissolved in butanone (7.8 l) and warmed to 30° C. Dess Martin periodinane (968 g; 2.28 mol) was added in portions. A short time after the addition of the first amounts a solid formed being the unsoluble by-products of the reagent. The temperature of the reaction mixture had increased to 43° C. upon complete addition. This temperature was maintained for 45 minutes. Dess Martin periodinane (242 g; 0.58 mol) was again added. Stirring was continued for 40 minutes. Then the volatiles were widely removed in vacuo and the residue was diluted with ethyl acetate (10 l). The solids were removed by filtration and washed with ethyl acetate (0.5 l). The combined filtrates of both runs were washed with saturated aqueous sodium bicarbonate solution (7 l) and saturated aqueous ammonium chloride solution (7 l). The combined aqueous layers were re-extracted with ethyl acetate (0.5 l). The combined organic layers were extracted three times with 1N hydrorochloric acid (4 l, 2×2 l). The combined aqueous layers was washed with ethyl acetate (100 ml). Ethyl acetate (7 l) was added to the aqueous layer, followed by the slow addition of 1 N sodium hydroxide solution (8 l) under vigorous stirring. At a pH between 4 to 5 the product went into the organic layer as indicated by a color switch of the layers. After complete addition, the pH value was 9. The layers were separated and the aqueous extracted with ethyl acetate (1 l). The combined organic layers were washed with water dried over sodium sulfate, filtered and evaporated. The crude product was obtained as a brown resin (783 g, chemical purity by HPLC at 230 nm=93.91%, chiral purity by HPLC (250 nm) is =98.47%) still containing 13 wt % of ethyl acetate, which has the following NMR data:

1H-NMR (CDCl3, 300 MHz) 8.58 (ddd, 1H, J=4.8, 1.7, 0.9); 8.19 (dt, 1H, J=7.9, 1.0); 7.8 (td, 1H, J=7.7, 1.8); 7.72 (dd, 1H, J=8.6, 2.3); 7.66 (d, 1H, J=2.3); 7.34 (ddd, 1H, J=7.6, 4.8, 1.2); 7.31 (d, 1H, J=8.6); 6.87 (dm, 1H, j=1.0) 4.09-4.02 (m, 1H); 3.68 (s, 3H); 2.9-2.7 (m, 4H); 2.35 (d 3H, J=1.0), which correspond to the compound of formula (F). The calculated molecular weight was 640 g/mol corresponding to a yield 76%.

EXAMPLE A6

Preparation of 3-[(4S)-8-bromo-1-methyl-6-(2-pyridinyl)-4H-imidazo[1,2-a][1,4]benzodiazepine-4-yl] propionic acid methyl ester of formula (F) using a combination of a catalytic amount TEMPO and hypochlorite as oxidizing agent followed by acidic cyclisation a) Formation of 3-[(S)-7-bromo-2-(2-oxo-propylamino)-5-pyridin-2-yl-3H-1,4-benzodiazepin-3-yl]-propionic acid methyl ester of formula (FK) in ethyl acetate/toluene

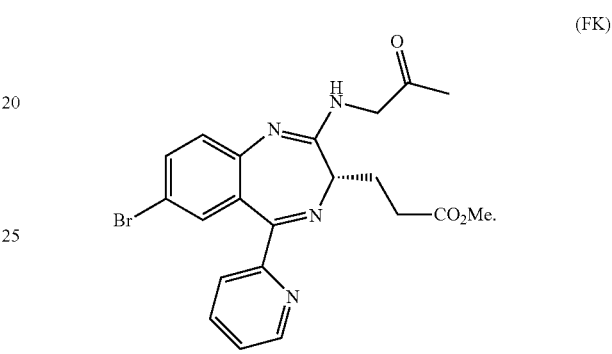

(FK)

230 mg (0.5 mmol) of the compound of formula (E) were dissolved in 1 ml of dichloromethane and cooled to less than 0° C. (in an ice/ethanol bath) giving a yellowish solution. 4.2 mg of sodium hydrogen carbonate (0.05 mmol) and 2.6 mg sodium bromide (0.025 mmol) were added. 0.78 mg (0.005 mmol) of TEMPO was added, immediately followed by 0.33 ml of a 2.1 mol/l NaOCl solution (0.7 mmol). The organic layer was colorless and the aqueous layer yellowish. The reaction mixture was stirred vigorously overnight. HPLC showed as main product a ketone and no presence of the compound of formula (E). The isolated main product showed the following NMR data:

1H-NMR (CDCl3, 300 MHz) 8.65 (ddd, 1H, J=4.8, 1.8, 0.8); 7.93 (dt, 1H, J=7.9, 1.0); 7.8 (td, 1H, J=7.7, 1.8); 7.52 (dd, 1H, J=8.6, 2.3); 7.41 (d, 1H, J=2.3); 7.36 (ddd, 1H, J=7.5, 4.8, 1.2); 7.2 (d, 1H, J=8.8); 4.25 (dd, 2H, J=90, 20); 3.71 (s, 3H) 3.36 (m, 1H); 2.85-2.40 (m, 4H); 2.21 (s, 3H), corresponding to the compound of formula (FK).

b) Cyclisation into the compound of formula (F)

1.83 g (4 mmol) of the compound of formula (FK) was dissolved in 15 ml chloroform. 76 mg (0.4 mmol) p-toluene sulfonic acid was added and the mixture was refluxed for 3 days. The reaction mixture was diluted with dichloromethane washed with sodium hydrogen carbonate solution, dried with magnesium sulphate and evaporated. The isolated main product showed the following NMR data:

1H-NMR (CDCl3, 300 MHz) 8.58 (ddd, 1H, J=4.8, 1.7, 0.9); 8.19 (dt, 1H, J=7.9, 1.0); 7.8 (td, 1H, J=7.7, 1.8); 7.72 (dd, 1H, J=8.6, 2.3); 7.66 (d, 1H, J=2.3); 7.34 (ddd, 1H, J=7.6, 4.8, 1.2); 7.31 (d, 1H, J=8.6); 6.87 (dm, 1H, j=1.0) 4.09-4.02 (m, 1H); 3.68 (s, 3H); 2.9-2.7 (m, 4H); 2.35 (d 3H, J=1.0), corresponding to the compound of formula (F).

EXAMPLE A7

Preparation of 3-[(4S)-8-bromo-1-methyl-6-(2-pyridinyl)-4H-imidazo[1,2-a][1,4]benzodiazepine-4-yl] propionic acid methyl ester benzene sulfonate (P) by one-pot cyclization of the compound of formula (FK) and salt formation 2 g (3.63 mmol) of the compound of formula (FK) were dissolved in 12 ml ethyl acetate at room temperature. 0.563 g (3.56 mmol) of benzene sulfonic acid was dissolved in 5.6 ml ethanol and added drop wise over 5 minutes to the reaction mixture. Precipitation. After 1 hour the solid was isolated by filtration, washed with ethyl acetate to give 1.09 g off-white solid, with the following NMR data:

1H-NMR (CDCl3, 300 MHz) 8.60 (ddd, 1H, J=4.8, 1.7, 0.9); 8.20 (dt, 1H, J=7.9, 1.0); 7.9 (m, 2H); 7.8 (m, 2H); 7.53 (d, 1H, J=1.2); 7.47 (d, 1H, J=8.8); 7.44-7.36 (m, 4H); 4.46-4.39 (m, 1H); 3.62 (s, 3H); 3.0-2.6 (m, 4H); 2.43 (s, 3H, J=1.0), corresponding to the compound (P). The chemical purity as determined by HPLC (230 nm) was 99.07% and the optical purity as determined by HPLC (290 nm) was 99.98%.

EXAMPLE A8

Preparation of 3-[(4S)-8-bromo-1-methyl-6-(2-pyridinyl)-4H-imidazo[1,2-a][1,4]benzodiazepine-4-yl] propionic acid methyl ester benzene sulfonate (P) from 3-[(4S)-8-bromo-1-methyl-6-(2-pyridinyl)-4H-imidazo[1,2-a][1,4]benzodiazepine-4-yl]propionic acid methyl ester of formula (F)

The crude compound of formula (F) (783 g residue from Example A5) was dissolved in ethyl acetate (3.8 l). A solution of benzenesulfonic acid (228 g, 1.44 mol) in ethanol (1.8 l) was added within 50 minutes under stirring. The resulting sticky yellow suspension was stirred for another 50 minutes. The solid was isolated by filtration, washed with ethyl acetate (0.6 l), then dried overnight at 45° C. and 125 mbar in a drying oven. Yield was 702 g (81%) of a white solid with a chemical purity as determined by HPLC (230 nm) was 99.35% and the optical purity as determined by HPLC (250 nm) was 99.91%, with the following NMR data:

1H-NMR (CDCl3, 300 MHz) 8.60 (ddd, 1H, J=4.8, 1.7, 0.9); 8.20 (dt, 1H, J=7.9, 1.0); 7.9 (m, 2H); 7.8 (m, 2H); 7.53 (d, 1H, J=1.2); 7.47 (d, 1H, J=8.8); 7.44-7.36 (m, 4H); 4.46-4.39 (m, 1H); 3.62 (s, 3H); 3.0-2.6 (m, 4H); 2.43 (s, 3H, J=1.0), corresponding to the compound (P).

What is claimed is:

1. A process for preparing 3-[(4S)-8-bromo-1-methyl-6-(2-pyridinyl)-4H-imidazo[1,2-a][1,4]benzodiazepine-4-yl] propionic acid methyl ester of formula (F)

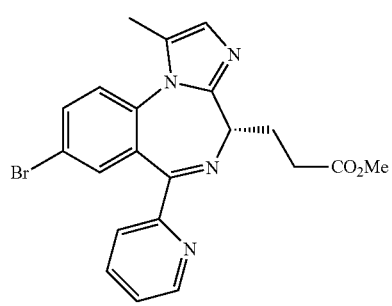

(F)

which comprises reacting 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM)

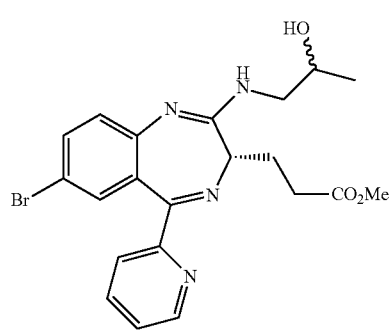

(EM)

with an oxidizing agent which is a hypervalent iodine compound of formula (DM)

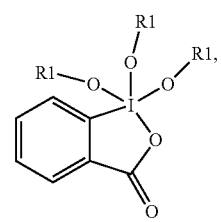

(DM)

wherein R1 is acyl.

2. The process of claim 1, wherein the compound of formula (EM) is 3-[(S)-7-bromo-2-((R)-2-hydroxy-propylamino)-5-pyridin-2-yl-3H benzo[e][1,4]diazepin-3-yl]-propionic acid methyl ester of formula (E)

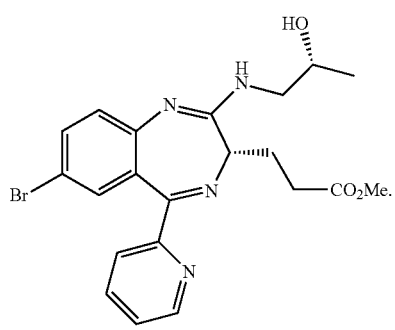

(E)

3. A process for preparing 3-[(4S)-8-bromo-1-methyl-6-(2-pyridinyl)-4H-imidazo[1,2-a][1,4]benzodiazepine-4-yl]-propionic acid methyl ester benzene sulfonate (P) which comprises the steps of,
(a) reacting 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM)

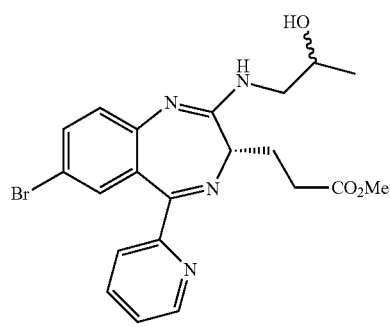

(EM)

with an oxidizing agent which is a hypervalent iodine compound of formula (DM)

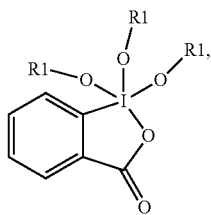

(DM)

wherein R1 is acyl, and
(b) treating the reaction product obtained in step (a) with benzene sulfonic acid in an organic solvent or an organic solvent mixture, to produce the compound (P), and optionally (c) isolating the compound (P).

4. The process of claim 3, wherein the compound of formula (EM) is 3-[(S)-7-bromo-2-((R)-2-hydroxy-propylamino)-5-pyridin-2-yl-3H-benzo[e][1,4]diazepin-3-yl]-propionic acid methyl ester of formula (E)

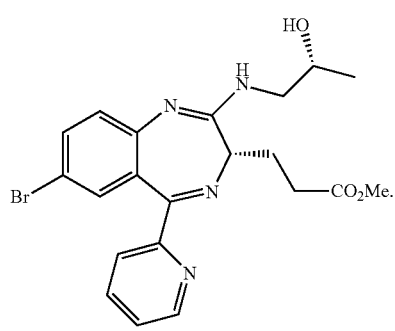

(E)

5. The process of claim 3, further comprising preparing 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM) by a method comprising reacting a compound of formula (E1)

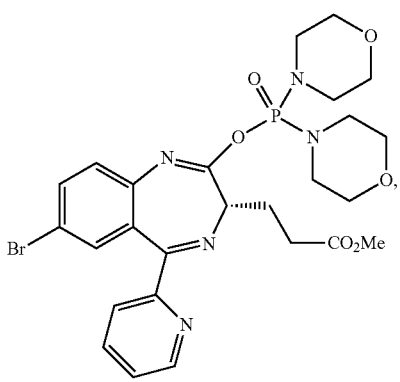

(E1)

with (R)-1-amino-2-propanol or (S)-1-amino-2-propanol.

6. The process of claim 5, characterized in that the compound of formula (E1) is reacted with (R)-1-amino-2-propanol.

7. The process of claim 3, wherein 3-[(S)-7-bromo-2-((R and/or S)-2-hydroxy-propylamino)-5-pyridin-2-yl-3H-benzo[e][1,4]diazepin-3-yl]-propionic acid methyl ester of formula (EM) is crystallised from a solvent or a solvent mixture.

8. The process of claim 5, further comprising preparing a compound of the formula (E1) by a method comprising reacting 3-[(S)-7-bromo-2-oxo-5-pyridin-2-yl-2,3-dihydro-1H-1,4-benzodiazepin-3-yl]propionic acid methyl ester of formula (D)

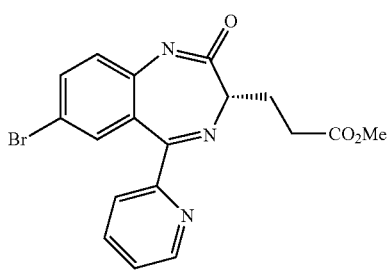

(D)

with lithium diisopropylamide (LDA) and bis-morpholinophosphorylchloridate (BMPC).

9. The process of claim 8, further comprising the step of preparing 3-[(S)-7-bromo-2-oxo-5-pyridin-2-yl-2,3-dihydro-1H-1,4-benzodiazepin-3-yl]-propionic acid methyl ester of formula (D) by a method comprising cyclizing the compound of formula (C)

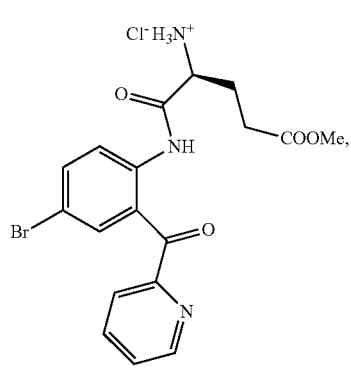

(C)

by the treatment with a base in an organic solvent or organic solvent mixture.

10. The process of claim 9, further comprising the step of preparing the compound of formula (C) by cleaving the 'Boc group from compound of formula (B)

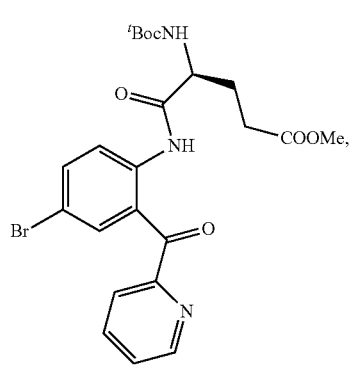

(B)

by treatment with hydrogen chloride.

11. The process of claim 10, further comprising the step of preparing the compound of formula (B) by treating (2-amino-5-bromo-phenyl)-pyridin-2-yl-methanone of formula (A)

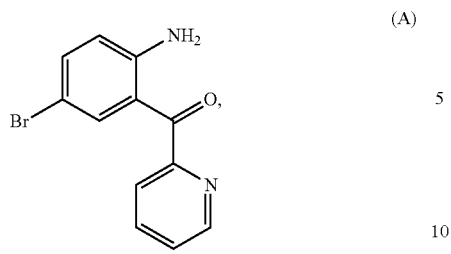

(A)

with ʳBoc-Glu(OMe)-OH in presence of a coupling agent.

12. The process of claim 7, wherein the solvent or solvent mixture is ethyl acetate, isobutylacetate, 2-propanol, toluene or ethyl acetate/heptane.

13. The process of claim 1, wherein the hypervalent iodine compound of formula (DM) is 1,1,1-triacetoxy-1,1-dihydro-1,2-benzoiodoxol-3(1H)-one (Dess-Martin periodinane).

14. The process of claim 3, wherein the hypervalent iodine compound of formula (DM) is 1,1,1-triacetoxy-1,1-dihydro-1,2-benzoiodoxol-3(1H)-one (Dess-Martin periodinane).

\* \* \* \* \*

UNITED STATES PATENT AND TRADEMARK OFFICE
CERTIFICATE OF CORRECTION

PATENT NO. : 9,156,842 B2  
APPLICATION NO. : 13/496742  
DATED : October 13, 2015  
INVENTOR(S) : Gary Stuart Tilbrook, Andreas Schumacher and Rene Emmenegger Page 1 of 1

It is certified that error appears in the above-identified patent and that said Letters Patent is hereby corrected as shown below:

Column 22, claim 8:

please replace:

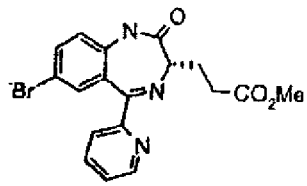

with:

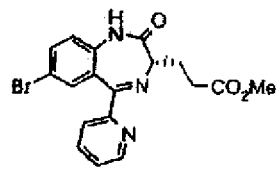

Signed and Sealed this  
Fifth Day of July, 2016

Michelle K. Lee  
*Director of the United States Patent and Trademark Office*